United States Patent

Gadwood et al.

Patent Number: 5,525,742
Date of Patent: Jun. 11, 1996

[54] AZIDOPHENYLCYANOGUANIDINES AS PHOTOAFFINITY PROBES

[75] Inventors: Robert C. Gadwood; Vincent E. Groppi, Jr., both of Kalamazoo, Mich.

[73] Assignee: The Upjohn Company, Kalamazoo, Mich.

[21] Appl. No.: 257,856

[22] Filed: Jun. 10, 1994

[51] Int. Cl.⁶ .................................................. C07C 279/28
[52] U.S. Cl. ................................................................ 552/8
[58] Field of Search ..................................................... 552/8

[56] References Cited

U.S. PATENT DOCUMENTS

| Re. 31,244 | 5/1983 | Petersen | 424/263 |
| 4,057,636 | 11/1977 | Petersen | 424/263 |
| 5,336,689 | 8/1994 | Weber et al. | 552/8 |

FOREIGN PATENT DOCUMENTS

| 405525A2 | 1/1991 | European Pat. Off. | C07C 279/28 |
| 9211233-A1 | 12/1990 | WIPO . | |

OTHER PUBLICATIONS

Mais, Dale E., et al., "Novel Synthesis and Biochemical Properties of an [$^{125}$I]–Labeled Photoaffinity Probe for Thromboxane A$_2$/Prostaglandin H$_2$ Receptors," *J. Med. Chem.*, 34, 4, pp. 1511–1514 (1991).

Petersen, Hans J., et al., "Synthesis and Hypotensive Activity of N–Alkyl–N–cyano–N'–pyridylguanidines," *J. Med. Chem.*, 21, 8, pp. 773–781 (1978).

*Primary Examiner*—Rebecca Cook
*Attorney, Agent, or Firm*—Thomas A. Wootton

[57] ABSTRACT

This invention comprises novel compounds that are useful and effective as photoaffinity probes useful for the identification of the biochemical components that form $K_{ATP}$ channels in smooth muscle cells. The probes are described by the formula below,

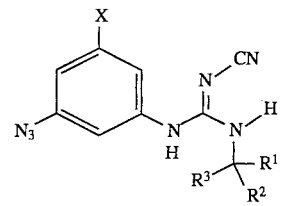

where $R_1$ is H, $C_{1-3}$ alkyl;

$R_2$ is H, $C_{1-3}$ alkyl; or $R_1$ and $R_2$ may be joined together to form $C_{3-6}$ cycloalkyl, or $C_{3-6}$ cycloalkyl optionally substituted with $C_{1-4}$ alkyl;

$R_3$ is $C_{1-6}$ alkyl, or $C_{6-12}$ aryl optionally substituted with 1–3 Halogens; or suitable salts thereof.

8 Claims, 6 Drawing Sheets

AZIDOPHENYLCYANOGUANIDINES AS PHOTOAFFINITY PROBES

FIELD OF THE INVENTION

This invention relates to radiolabeled photolabile molecules useful for biochemical characterization of receptors. The radiolabeled photolabile molecules of this invention are azidophenylcyanoguanidines.

INFORMATION DISCLOSURE

The following documents are related to the disclosure herein. Mais, Dale E., et. al., "Novel Synthesis and Biochemical Properties of an [$^{125}$I]-Labeled Photoaffinity Probe for Thromboxane $A_2$/Prostaglandin $H_2$ Receptors," J. Med. Chem., 34, 4, pp. 1511–1514 (1991). Petersen, Hans J., et. al., "Synthesis and Hypotensive Activity of N-Alkyl-N''-cyano-N'-pyridylguanidines," J. Med. Chem., 21, 8, pp. 773–781 (1978). U.S. Pat. No. Re. 31,244, reissued May 17, 1983, "Antihypertensive Pyridylguanidine Compounds," H. J. Petersen. U.S. Pat. No. 4,057,636, issued Nov. 8, 1977, "Antihypertensive Pyridylguanidine Compounds," H. J. Petersen. WO 9211233-A1, published 90.12.19, "New aryl:cyano:guanidine potassium channel dilater—for treating hypertension," assigned to Kanebo Ltd. European Patent 405 525 A2, published 02.01.91, "Novel Cyanoguanidine Derivatives," M. Tominori.

BACKGROUND

The ATP-sensitive, or ATP-gated potassium channels play an important role in human physiology. The ATP-sensitive potassium channel, like other potassium channels, selectively regulate the cell's permeability to potassium ions. These channels function to regulate the contraction and relaxation of the smooth muscle by opening or closing the channels in response to the modulation of receptors or potentials on the cell membrane. When ATP-sensitive potassium channels are opened, the increased permeability of the cell membrane allows more potassium ions to migrate outwardly so that the membrane potential shifts toward more negative values. Once this has occurred, the opening of the voltage-dependent calcium channels would be reduced, which in turn reduces the influx of calcium ions into the cell because the calcium channels become "increasingly less open" as the membrane potential becomes more negative. Consequently, drugs having ATP-sensitive potassium channel opening activity, drugs known as potassium channel openers, can relax vascular smooth muscle and are useful as hypotensive and coronary vasodilating agents.

A relatively large number of compounds are now known which open cell membrane ATP-sensitve potassium channels, particularly in smooth muscle: minoxidil sulfate, diazoxide and nicorandil are well known potassium channel openers. The target site for these agents is presumably on the potassium channel itself, but may also be on an associated regulatory protein. Isolation of the target site for the potassium channel openers would allow for protein sequence analysis and cloning of those potassium channel opener proteins. This would make possible new assays for molecules that interact with the potassium channel opener site.

One technique for the biochemical characterization of receptors is photoaffinity labeling using a radiolabeled photolabile molecule, or probe, which binds with high affinity to a receptor and can be irreversibly incorporated into the receptor under the influence of ultraviolet light.

In order to have an effective and useful photoaffinity probe, several requirements must be met. First, the probe must have good biological activity at the same target protein relative to the parent compounds of interest. Second, it must have a reactive group which can covalently bond to the target site upon photoactivation. Third, it must have a radioactive or fluorescent label by which the probe-target complex can be identified. Surprisingly and unexpectedly, the compounds of this invention satisfy the requirements of an effective and useful photoaffinity probe.

SUMMARY OF THE INVENTION

This invention comprises novel compounds that are useful and effective as photoaffinity probes useful for the identification of the biochemical components that form $K_{ATP}$ channels in smooth muscle cells. The probes are described by Formula I,

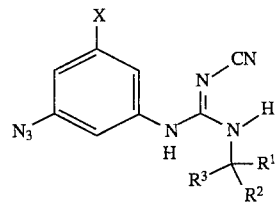

Formula I where $R_1$ is H, $C_{1-3}$ alkyl;

$R_2$ is H, $C_{1-3}$ alkyl; or $R_1$ and $R_2$ may be joined together to form $C_{3-6}$ cycloalkyl, or $C_{3-6}$ cycloalkyl optionally substituted with $C_1$–$C_4$ alkyl;

$R_3$ is $C_1$–$C_6$ alkyl, or $C_{6-12}$ aryl optionally substituted with 1–3 Halogens;

or suitable salts thereof. The invention also comprises compounds described by Formula II,

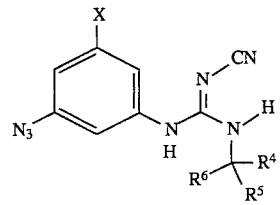

Formula II where

X is Halogen;

$R_4$ is H, $C_{1-3}$ alkyl;

$R_5$ is H, $C_{1-3}$ alkyl;

$R_4$ and $R_5$ may be joined together to form $C_{3-6}$ cycloalkyl, or $C_{3-6}$ cycloalkyl optionally substituted with $C_1$–$C_4$ alkyl;

$R_6$ is a $C_{6-12}$ aryl optionally substituted with $C_{1-2}$ alkyl, or 1–3 Halogens;

or suitable salts thereof.

Methods of using the probes, their process, manufacture, and compositions are also described and or claimed.

DETAILED DESCRIPTION OF THE INVENTION

Figure 1:
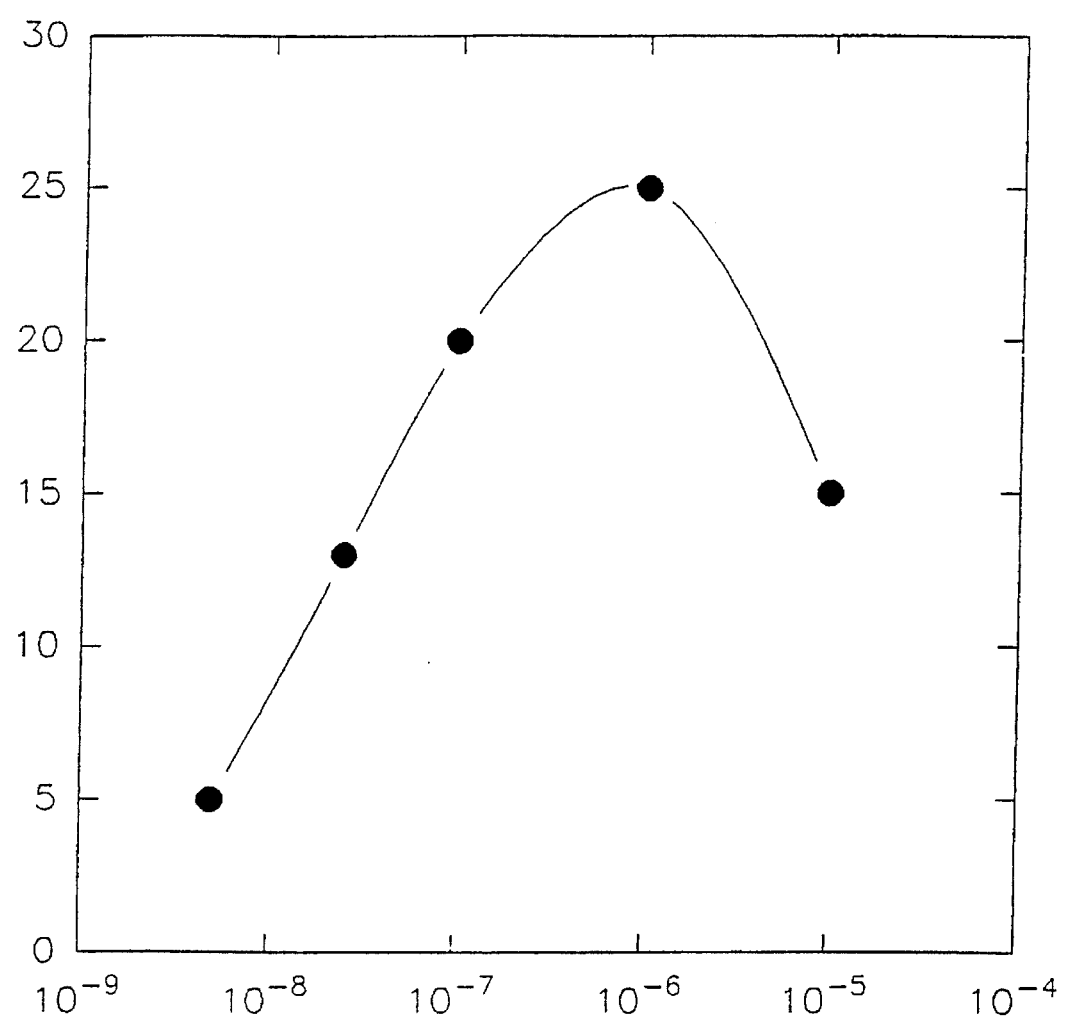
FIG. 1. The concentration response curve for the effect of N-cyano-N'-(1,1-dimethylpropyl)-N''-3-pyridinyl-guanidine, a $K_{ATP}$ channel opener, on the resting membrane potential of A10 smooth muscle cells.

Terms and Descriptions. The compounds of this invention are identified in two ways: by descriptive names and by reference to chemical formulas containing various chemical moieties. In appropriate situations, the proper stereochemistry is also represented in the chemical formulas. The following terms may also be used to describe this invention.

OPTIONALLY SUBSTITUTED The term "optionally substituted" shall mean a group or radical that is substituted with halogen, lower alkyl, mono- or di(lower alkyl)-substituted lower alkyl.

ALKYL The parenthetical term ($C_{n-m}$ alkyl) is inclusive such that a compound of ($C_{1-8}$) would include compounds of 1 to 8 carbons and their isomeric forms. The various carbon moieties are aliphatic hydrocarbon radicals and includes branched or unbranched forms such as methyl, ethyl, n-propyl, isopropyl, n-butyl, isobutyl, sec-butyl, t-butyl, n-pentyl, isopentyl, n-hexyl, isohexyl, n-heptyl, isoheptyl, and n-octyl and isomeric forms thereof.

n-ALKYL The parenthetical term ($C_{n-m}$ n-alkyl) is inclusive such that a compound of ($C_1$–$C_8$) would include compounds of 1 to 8 carbons in their straight chain unbranched form.

CYCLOALKYL The parenthetical term ($C_{n-m}$ cycloalkyl) is inclusive such that a compound of ($C_{3-10}$) would include radicals of a saturated cyclic hydrocarbon of 3 to 10 carbons in their cyclic chain. The term may also include alkyl-substituted cycloalkyl, such as cyclopropyl, 2-methylcyclopropyl, 2,2-dimethylcyclopropyl, 2,3 diethylcyclopropyl, 2-butylcyclopropyl, cyclobutyl, 2-methylcyclobutyl, 3-propylcyclobutyl, cyclopentyl, 2,2-dimethylcyclopentyl, cyclohexyl, cycloheptyl, cyclooctyl and cyclodecyl and the like. Each of these moieties may be substituted as appropriate.

ARYL Aryl refers to a 6 to 12 carbon atom base structure, one or two fused or nonfused aromatic rings. Aryl may be optionally substituted or substituted with one to 3 hydroxy, $C_1$–$C_3$ alkoxy, $C_1$–$C_3$ alkyl, trifluoromethyl, fluoro, chloro, or bromo groups. Examples of "aryl" are: phenyl, m-methylphenyl, p-trifluoromethylphenyl, α-naphthyl, β-naphthyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)-tolyl, 4-isopropyl-2,6-xylyl, 3-propyl-4-ethylphenyl, (2,3,4-, 2,3,6-, or 2,4,5-)trimethylphenyl, (o-, m-, or p-)fluorophenyl, (o-, m-, or p-trifluoromethyl)phenyl, 4-fluoro-2,5-xylyl, (2,4-, 2,5-, 2,6-, 3,4-, or 3,5-) difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-)chloro-2-fluorophenyl, (o-, m-, or p-,)trifluorophenyl, (o-, m-, p-)ethoxyphenyl, (4- or 5-)chloro-2-methoxyphenyl, and 2,4-dichloro(5- or 6-)methylphenyl and the like. Each of these moieties may be substituted as appropriate.

CHIRALITY It will be apparent to those skilled in the art that compounds of this invention may contain one or more chiral centers and may exist in optically active forms including cis-/trans- and/or R- and S- isomeric forms and mixtures thereof. The scope of this invention includes all of these forms, the enantiomeric or diastereomeric forms, of the compounds, including optically active forms, in pure form or as mixtures of enantiomers or diastereomers including cis-/trans-isomeric forms. The therapeutic properties of the compounds may to a greater or lesser degree depend on the stereochemistry of a particular compound.

HALOGEN The term "halo-" and "halogen" refer to substituents selected from fluoro, chloro, bromo, iodo or trifluoromethyl.

One ordinarily skilled in the art would know how to use the compounds of this invention without further details. Reference to standard texts and review articles is expected. The following details and embodiments concerning assays, measures of activity and specific responses of $K_{ATP}$ channels are provided only for illustration and completeness and are not intended to limit the invention in any manner. Related uses can be found by refering to the articles disclosed in the "Information Disclosure" above, those articles are incorporated by reference herein.

I. ASSAY OF $K_{ATP}$ CHANNEL MODULATORS.

Compounds that modulate $K_{ATP}$ channel activity were examined by quantitating the effect of these compounds on the resting membrane potential of A10 rat aortic smooth muscle cells (American Type Culture Collection, number CRL-1476) using a fluorescent, potentialsensitive dye and an instrument to measure changes in cellular fluorescence. The dye of choice is bis(1,3-dibutylbarbituric acid)trimethine oxonol) $DiBAC_4(3)$. Other voltage sensitive dyes could also be used. To optically measure changes in membrane potential, cells were subcultured onto coverglass chambers and grown to confluence. Immediately prior to analysis, cells were washed several times with Earle's balanced salt solution that was buffered to pH 7.4 with 20 mM Hepes (EBSS-H) and then placed in the buffer containing 5 μM $DiBAC_4(3)$. Fluorescent imaging of membrane potential was carried out after the cells were equilibrated with 5 μM $DiBAC_4(3)$ for at least 15 min at 37° C. and then placed in a 35° C. temperature-regulated mini-incubator that was mounted on the stage of laser based imaging cytometer (ACAS 570, Meridian Instruments). The ACAS 570 was configured to excite the cells at 488 nm using an argon ion laser. The fluorescent emission was monitored at 525 nm. To determine the effect of azidophenylcyanoguanidines on membrane potential, the ACAS 570 was configured to collect data once every 60 seconds for at least 25 minutes using the Kinetic program within the ACAS software. In all cases, 7 min. of baseline data were collected before the addition of the compound of interest. Changes in membrane potential were computed using a logistical model developed at Upjohn Laboratories. Control experiments established that solvents such as dimethylsulfoxide and ethanol had no effect at concentrations up to 0.8%. Previous studies by Epps et. al. (Chemistry of Physics and Lipids 69:137–150, 1994) established that there is a linear relation between changes in membrane potential and changes in cellular fluorescence indicating that the optical membrane potential assay is quantitative.

Figure 2:
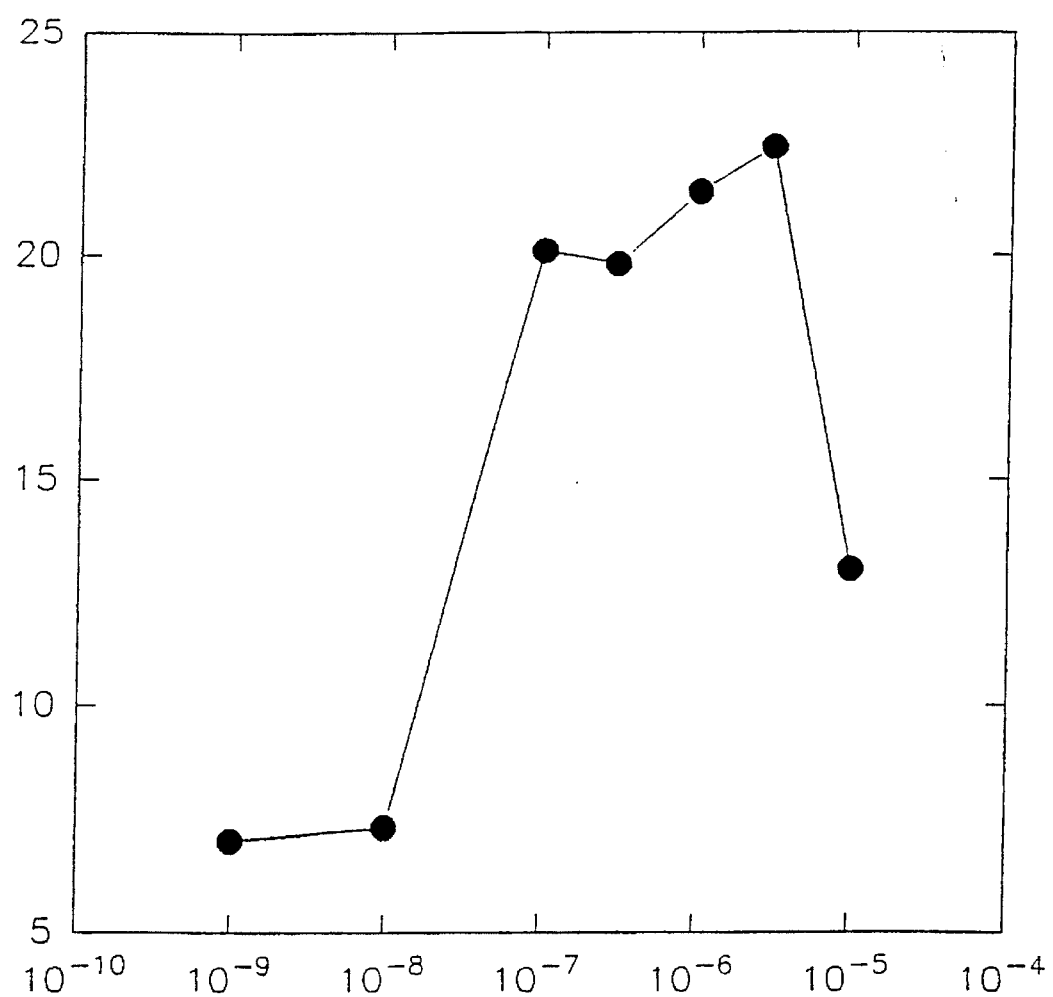
FIG. 2. The concentration response curve for the effect of Example 1, a $K_{ATP}$ channel opener, on the resting membrane potential of A10 smooth muscle cells.
Figure 3:
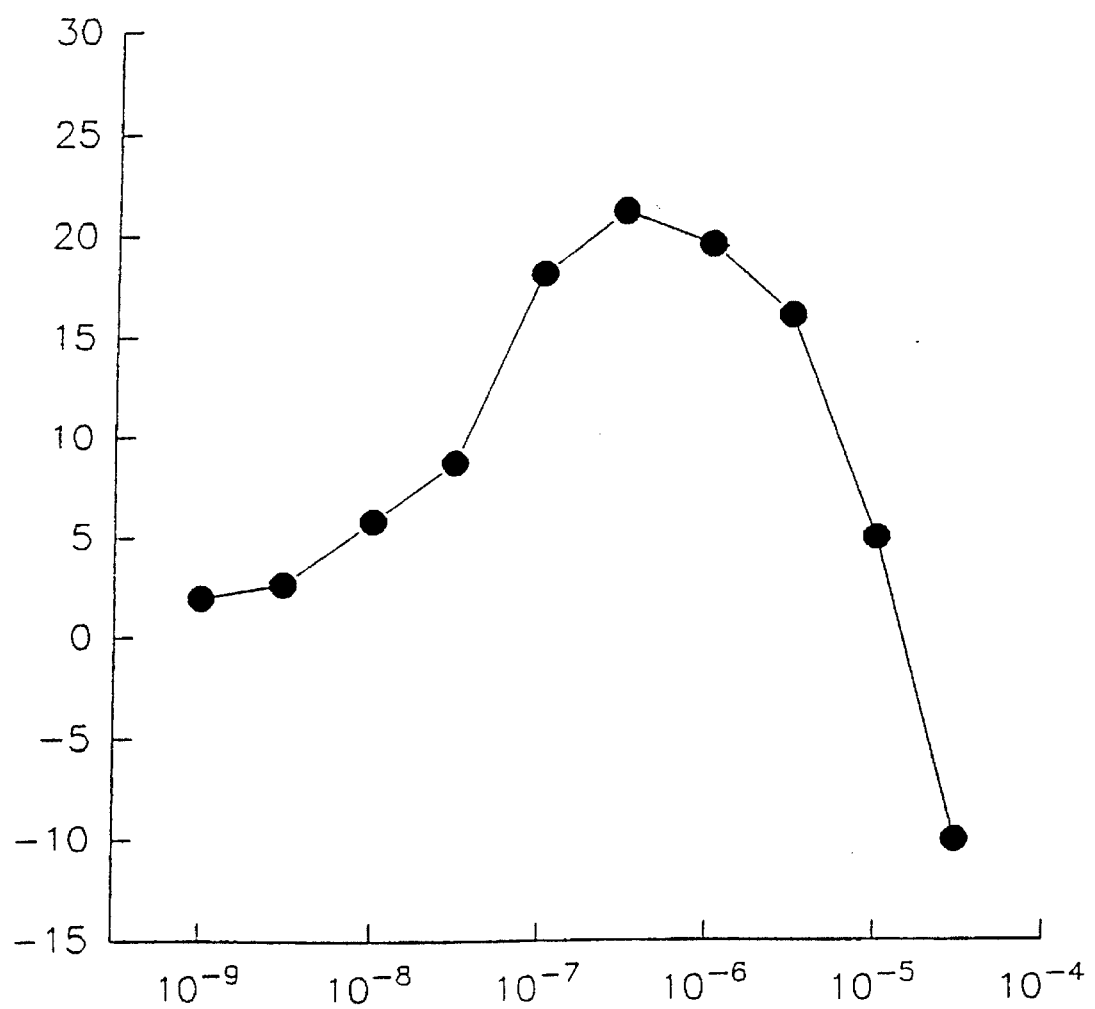
FIG. 3. The concentration response curve for the effect of Example 2, a $K_{ATP}$ channel opener, on the resting membrane potential of A10 smooth muscle cells.

The data in FIG. 1 shows the concentration response of N-cyano-N'-(1,1-dimethylpropyl)-N"-3-pyridinylguanidine on the membrane potential of A10 cells. In FIG. 1 the Y axis represents the change in membrane potential elicited by N-cyano-N'-(1,1-dimethylpropyl)-N"-3-pyridinylguanidine. A positive change represents a hyperpolarization of the membrane potential caused by an opening of a $K_{ATP}$ channel. The X axis represents increasing concentrations of N-cyano-N'-(1,1-dimethylpropyl)-N"-3-pyridinylguanidine. N-cyano-N'-(1,1-dimethylpropyl)-N"-3-pyridinylguanidine, which is also known as P1075, is one of the most potent cyanoguanidine $K_{ATP}$ openers known. The $EC_{50}$ for N-cyano-N'-(1,1-dimethylpropyl)-N"-3-pyridinylguanidine in the A10 membrane potential assay is 30 nM. The data in FIG. 2 shows the concentration response of Example 1 on the membrane potential of A10 cells. In FIG. 2 the Y axis represents change in membrane potential elicited by Example 1. A positive change represents a hyperpolarization of the membrane potential caused by an opening of a $K_{ATP}$ channel. The X axis represents increasing concentrations of Example 1. Example 1 is structurally related to N-cyano-N'-(1,1-dimethylpropyl)-N"-3-pyridinylguanidine and has an $EC_{50}$ of approximately 30 nM in the A10 assay. The data FIG. 3 shows the concentration response of Example 2 on the membrane potential of A10 cells. In FIG. 3 the Y axis represents the change in membrane potential elicited by Example 2. A positive change represents a hyperpolarization of the membrane potential caused by an opening of a $K_{ATP}$ channel. The X axis represents increasing concentrations of Example 2. Example 2 is structurally related to N-cyano-N'-(1,1-dimethylpropyl)-N"-3-pyridinylguanidine and has an $EC_{50}$ of approximately 30 nM in the A10 assay. These data indicate that Example 1 and Example 2, two azidophenylcyanoguanidines, are as potent as N-cyano-N'-(1,1-dimethylpropyl)-N"-3-pyridinylguanidine in the A10 membrane potential assay. The effects of N-cyano-N'-(1,1-dimethylpropyl)-N"-3-pyridinylguanidine, Example 1 and Example 2 were blocked by 10 µM glyburide, which strongly indicates that these compounds are hyperpolarizing the A10 cell's membrane potential by opening a $K_{ATP}$ channel (data not shown). Taken together, these data strongly indicate that Example 1 and Example 2 fulfill our first requirement for an effective photoprobe for the $K_{ATP}$ channel.

Figure 4A:
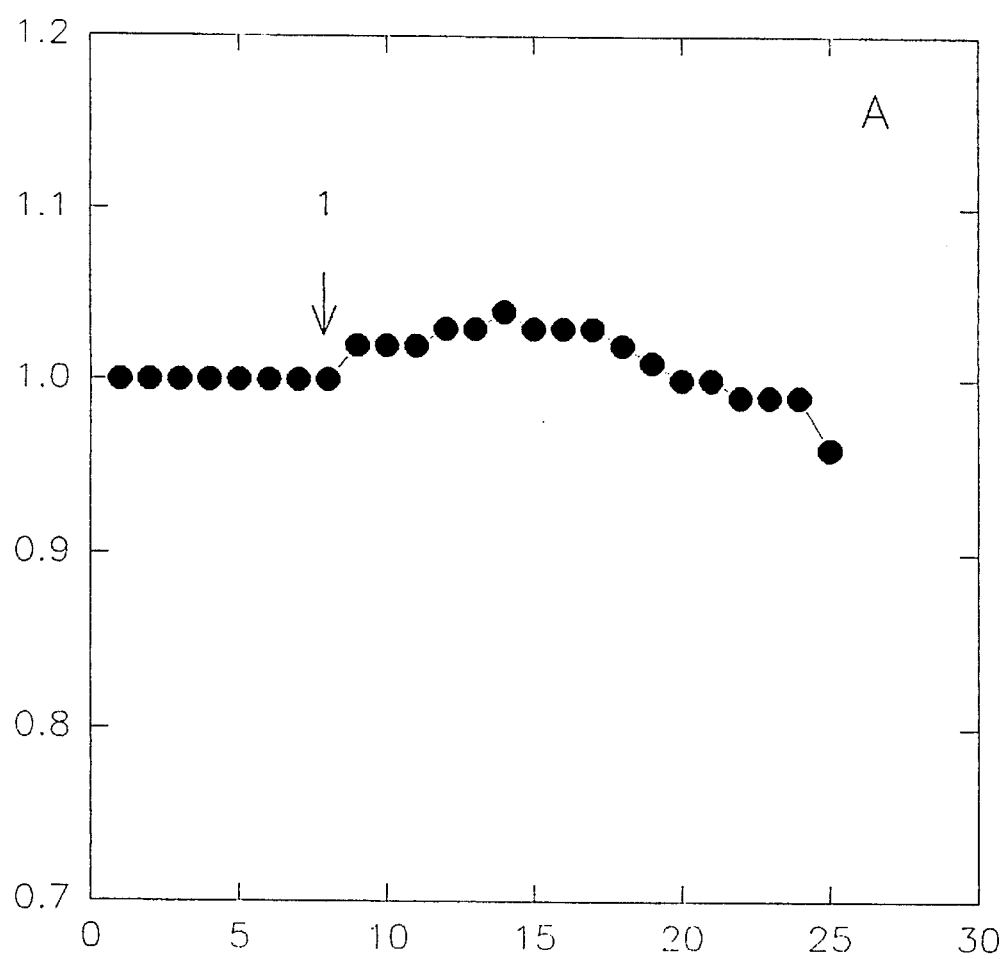
FIG. 4. Example 3, a $K_{ATP}$ channel blocker, reverses the effect of N-cyano-N'-(1,1-dimethylpropyl)-N"-3-pyridinyl-guanidine in A10 smooth muscle cells.
Figure 4B:
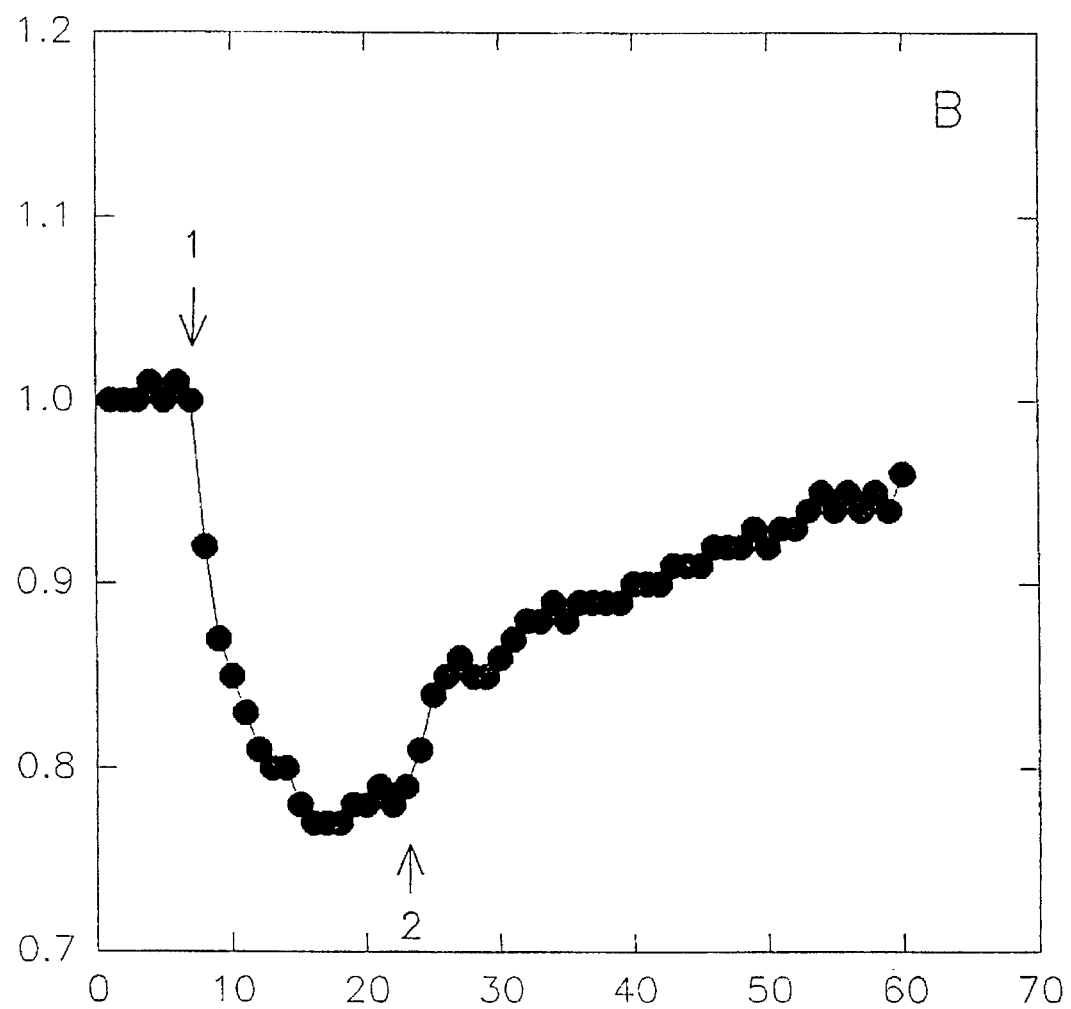

The data in FIG. 4A indicates that the addition of 10 µM Example 3 to A10 cells (arrow 1) has no effect on the membrane potential of A10 cells. In FIG. 4A and 4B the Y axis represents a change in membrane potential. In these experiments, a change in the negative direction represents a hyperpolarization of the membrane potential caused by an opening of a $K_{ATP}$ channel. In FIG. 4A and 4B the X axis represents time in minutes. Additional experiments indicate that 0.3 and 1.0 µM Example 3 also have no effect on the membrane potential of A10 cells (data not shown). These data clearly indicate that Example 3 has no effect on the resting membrane potential of A10 cells and therefore Example 3 is not a $K_{ATP}$ channel opener in the A10 cell assay. The data in FIG. 4B indicates that the addition of 1 µM N-cyano-N'-(1,1-dimethylpropyl)-N"-3-pyridinylguanidine (arrow 1) opens the A10 $K_{ATP}$ channel, causing a concomitant hyperpolarization of the membrane potential of these cells. When 10 µM Example 3 is added to A10 cells (arrow 2) in the continuing presence of 1 µM N-cyano-N'-(1,1-dimethylpropyl)-N"-3-pyridinylguanidine, we find that Example 3 reverses the effect of N-cyano-N'-(1,1-dimethylpropyl)-N"-3-pyridinylguanidine. Additional experiments indicate that Example 3 blocks the N-cyano-N'-(1,1-dimethylpropyl)-N"-3-pyridinylguanidine-dependent opening of $K_{ATP}$ channels in a concentration dependent manner. Taken together these data indicate that Example 3 is acting as a blocker of the $K_{ATP}$ channel in A10 cells. Thus, within the azidophenylcyanoguanidine chemical series there are compounds that can be used to identify the cellular components required to open and close $K_{ATP}$ close channels.

II. PHOTOINACTIVATION OF $K_{ATP}$ CHANNELS

Photoinactivation of $K_{ATP}$ channels in A10 cells was carried out on cells grown on coverglass chambers. A10 cells were grown to confluence and washed 3 times with EBSS-H. The A10 cells were then equilibrated for 15 min at 37° C. with 100 nM to 30 µM of the azidophenyl-cyanoguanidines. The A10 cells were exposed to 600 µwatts/cm² of 254 nm light for 1 min to photoactivate these azidophenyl-cyanoguanidines. After photolysis, the A10 cells were extensively washed with EBSS-H and finally placed in EBSS-H containing 5 µM $DiBAC_4(3)$. The pretreated cells were then challenged with 1 µM N-cyano-N'-(1,1-dimethylpropyl)-NΔ-3-pyridinylguanidine and changes in membrane potential were measured as described in Section I, above, ASSAY OF $K_{ATP}$ CHANNEL MODULATORS. If the $K_{ATP}$ channels in A10 cells were covalently photoinactivated by the azidophenyl-cyanoguanidines, then the cells would be unresponsive to the subsequent challenge of $K_{ATP}$ openers such as N-cyano-N'-(1,1-dimethylpropyl)-N"-3-pyridinylguanidine. On the other hand, if the $K_{ATP}$ channels in A10 cells were not covalently photoinactivated by the azidophenyl-cyanoguanidines, then the cells would be responsive to a subsequent challenge of $K_{ATP}$ openers such as N-cyano-N'-(1,1-dimethylpropyl)-N"-3-pyridinylguanidine.

Figure 5:
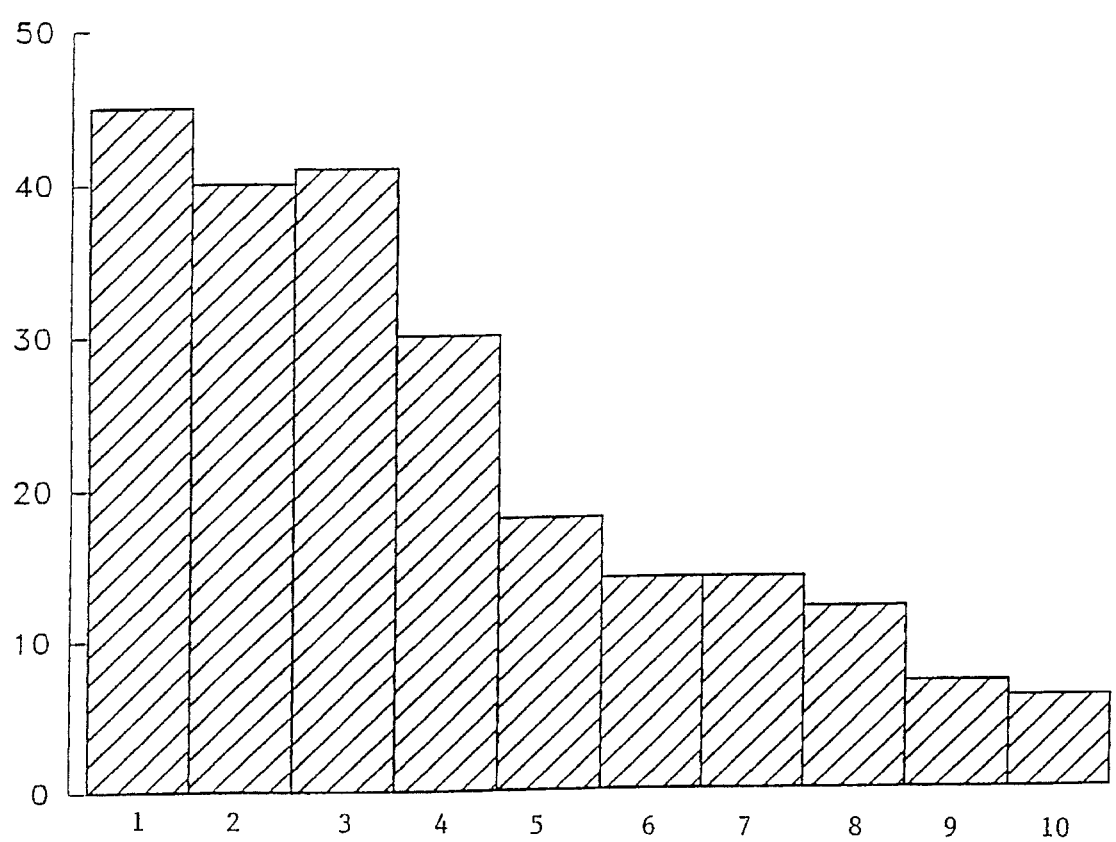
FIG. 5. Photoinactivation of $K_{ATP}$ channels in A10 smooth muscle cells by Example 1 and UV light.

The data in FIG. 5 indicate the effects of Example 1 and UV light on the $K_{ATP}$ channel in A10 cells. In FIG. 5, the Y axis represents the change in membrane potential elicited by challenging cells with 1 µM N-cyano-N'-(1,1-dimethylpropyl)-N"-3-pyridinylguanidine after pretreatment. In FIG. 5, a change in the positive direction indicates a hyperpolarization of the membrane potential caused by an opening of a $K_{ATP}$ channel. The X axis represents pretreatment conditions. In lane 1, the A10 cells were maintained in the standard EBSS-H solution. In lane 2, the A10 cells were pretreated with the solvent (0.1% dimethylsulfoxide) and UV light. Lane 2 represents the solvent and UV control. In lane 3, the A10 cells were pretreated with N-cyano-N'-(1,1-dimethylpropyl)-N"-3-pyridinylguanidine and UV light. N-cyano-N'-(1,1-dimethylpropyl)-N"-3-pyridinylguanidine contains no photoactivatable chemical groups and thus should not covalently modify the $K_{ATP}$ channel. In lane 4, the A10 cells were exposed to 100 nM Example 1 and UV light. In lane 5, the A10 cells were exposed to 250 nM Example 1 and UV light. In lane 6, the A10 cells were exposed to 500 nM Example 1 and UV light. In lane 7, the A10 cells were exposed to 1 µM Example 1 and UV light. In lane 8, the A10 cells were exposed to 2.5 µM Example 1 and UV light. In lane 9, the A10 cells were exposed to 5 µM Example 1 and UV light. In lane 10, the cells were exposed to 10 µM Example 1 and UV light.

The data in FIG. 5 indicate that A10 cells exposed to UV light in the presence of the solvent, dimethylsulfoxide, or N-cyano-N'-(1,1-dimethylpropyl)-N"-3-pyridinylguanidine, a compound that does not contain a photoactivatable chemical group, remain nearly completely responsive to a second challenge of N-cyano-N'-(1,1-dimethylpropyl)-N"-3-pyridinylguanidine. In contrast, A10 cells pretreated with Example 1 and UV light show a concentration dependent loss of N-cyano-N'-(1,1-dimethylpropyl)-N"-3-pyridinylguanidine responsiveness. These data strongly indicate that Example 1 in the presence of UV light forms a covalent bond with one or more compounds of the $K_{ATP}$ channel of A10 cells. The identical experiments were carried out using Example 2 in place of Example 1. A10 cells pretreated with a maximum concentration of Example 1 or Example 2 and UV light remained responsive to agents that open the calcium-activated potassium channel. These experiments clearly demonstrate that both Example 1 and Example 2 specifically photoinactivated the A10 $K_{ATP}$ channel. We therefore conclude that Example 1 and Example 2 fulfill our second requirement for an effective photoprobe.

III. PHOTOLABELING OF CYANOGUANIDINE BINDING PROTEINS.

To biochemically identify the proteins that specifically bind the azidophenylcyanguanidines, Example 1a, Example 2a and Example 3a were prepared. A10 cells were grown to confluence in standard culture plates and then washed extensively with EBSS-H. After the final wash, the cells were placed in EBSS-H containing one of the radiolabeled forms of the azidophenylcyanguanidine to be tested. The A10 cells were equilibrated with the radiolabeled compound for 15 minutes at 37° C. The A10 cells were placed on ice and exposed for 1 minute to 600 μwatts/cm² of 254 nm UV light. After photolysis, the A10 cells were washed extensively with phosphate buffered saline. Membranes from the A10 cells were solubilized in cocktail of 0.2% Triton X100 detergent and protease inhibitors. The membranes were precipitated with 4 volumes of ice cold acetone for 30 minutes. The precipitate membrane proteins were collected by centrifugation at 20,000 rpm for 30 rain at 4° C. in a Beckman SW-28 rotor. After centrifugation the supernate was discarded and the pellet was dissolved 2% sodium dodecyl sulfate (SDS) as described by O'Farrell (J. Biol. Chem. 250:4007–4021, 1975). The radiolabeled proteins were resolved on an SDS polyacrylamide gel and identified by autoradiography after the gel was stained and dried.

Membrane extracts from A10 cells treated with Example 1a and UV light contain several radiolabeled proteins. The most prominent radiolabeled protein had an apparent molecular weight of 47 kilodaltons. When Example 1a was mixed with increasing concentration of nonradiolabeled Example 1 (30 nM to 30 uM), the radiolabeling of the 47 kilodalton protein was specifically inhibited. Control experiments established that no proteins were labeled in the absence of UV light. Membrane extracts from A10 cells treated with Example 2a and UV light contained the same 47 kilodalton protein that was radiolabeled by Example 1a and UV light. Membrane extracts from A10 cells treated with Example 2a and UV light also contained a 56 kilodalton protein. When Example 2a was mixed with increasing concentration of nonradiolabeled Example 2 (1 nM to 30 uM), the radiolabeling of the 47 kilodalton protein and 56 kilodalton protein was specifically inhibited. These data indicate that Example 1a and Example 2a, two $K_{ATP}$ channel openers, specifically radiolabel a 47 and 56 kilodalton protein. The specificity of the photolabeling reaction with Example 1a and Example 2a indicate that these compounds fulfill our third requirement for an effective photoprobe.

Membrane extracts from A10 cells treated with Example 3a and UV light contain several radiolabeled proteins that were not present in extracts prepared from cells treated with Example 1a and Example 2a. The most prominent protein had an apparent molecular weight of 37 kilodaltons. There was also a 27 kilodalton protein that was radiolabeled by Example 3a and UV light. When Example 3a was mixed with increasing concentration of nonradiolabeled Example 3 (1 nM to 30 uM), the radiolabeling of the 37 kilodalton protein and 27 kilodalton protein was specifically inhibited. These data indicate that Example 3a, which is a $K_{ATP}$ channel blocker, specifically labels a unique set of proteins that are different from the proteins radiolabeled by the photoactivable $K_{ATP}$ channel openers. The specificity of the photolabeling reaction with Example 3a indicates that this compound fulfills our third requirement for an effective photoprobe.

PREFERRED COMPOUNDS

Example 2, N-(3-azido-5-iodophenyl)-N'-cyano-N"-(1,1-dimethylpropyl)guanidine (See CHART B, B-2, X is I) and example 2(a), N-(3-azido-5-iodo-$^{125}$I-phenyl)-N'-cyano-N"-(1,1-dimethylpropyl)guanidine, are preferred compounds and so are example 3, N-(3-azido-5-iodephenyl) -N'-cyano-N"-[1-(3-fluorophenyl)cyclobutyl]guanidine and example 3(a), N-(3-azido-5-iodo-$^{125}$I-phenyl)-N'-cyano-N"-(1-(3-fluorophenyl)cyclobutyl)guanidine.

This invention comprises novel compounds that are useful and effective as photoaffinity probes useful for the identification of the biochemical components that form $K_{ATP}$ channels in smooth muscle cells. The identification of these biochemical components requires that the probes be used with intact cells or intact tissue. See the previous sections, II. PHOTOINACTIVATION OF $K_{ATP}$ CHANNELS and III PHOTOLABELING OF CYANOGUANIDINE BINDING PROTEINS, above.

PREPARATION OF THE COMPOUNDS

The compounds of this invention can be prepared by following the procedures and descriptions of the reactions of CHARTS A and B. The final product from CHART A is used as a starting material in CHART B. General enabling descriptions and procedures are provided below, followed by the CHARTS containing structural representations, followed by specific embodiments which represent and illustrate the invention.

SUMMARY OF THE REACTIONS

CHART A

The required 3-azido-5-haloanilines (A-4) can be prepared by the route shown in CHART A. Selective protection of a 5-halo-1,3-benzenediamine (A-1) with di-tert-butyl dicarbonate (BOC$_2$O), Step A-2, affords the intermediate carbamate (A-2). Step A-3, conversion to the azide (A-3) is accomplished under standard diazotization conditions and deprotection. Step A-4, with trifluoroacetic acid produces the 3-azido-5-haloaniline (A-4). The required alkylamines are commercially available or can be prepared by common procedures available from the chemical literature.

CHART B

Starting with the products from the reactions of CHART A, the final products can be prepared by the general procedures shown in CHART B, where X=halogen. Step B-1, reaction of a 3-azido-5-haloaniline (A-4) with diphenyl cyanocarbonimidate at 70°–75 ° C. affords the phenyl carbamimidate B-1. Subsequent reaction, Step B-2, of B-1 with the desired primary alkylamine in refluxing isopropanol leads to the cyanoguanidines (B-2).

CHART A

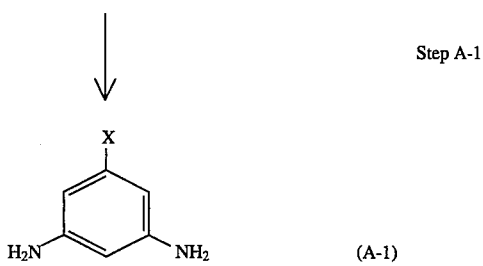

Step A-1

(A-1)

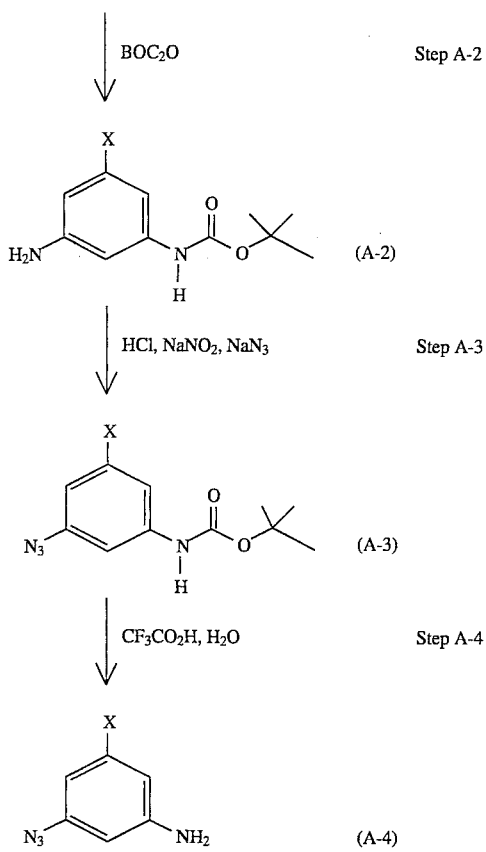

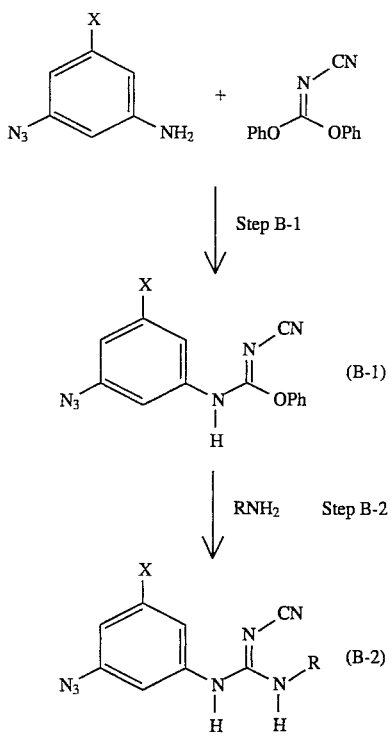

Using the above description one ordinarily skilled in the art can make and use the compounds of this invention. Specific embodiments of the invention are provided below. Structures and names of the embodied compounds are found summarized in CHART C. The examples below serve to illustrate the invention and are not intended to limit the invention in any manner.

Example 1. Synthesis of N-(3-azido-5-chlorophenyl)-N'-cyano-N''-(1,1dimethylpropyl)guanidine.

Chart A. Step A-2. A stirred solution of 5-chloro-1,3-phenylenediamine (A-1, X is Cl, 1.93 g, 13.5 mmol) in 55 mL of dichloromethane is cooled to 0° C. and di-tert-butyl dicarbonate (2.96 g, 13.5 mmol) is added. The reaction mixture is stirred at 20°–25° C. for 5 days and then concentrated. The residue is purified by medium pressure liquid chromatography using 25% ethyl acetate in hexane to afford 2.20 g of 3-amino-5-chlorophenylcarbamic acid, 1,1-dimethylethyl ester. (A-2) mp 85°–87 ° C.; IR (mull) 3439, 3357, 3328, 2926, 1691, 1613, 1589, 1524, 1475, 1438, 1391, 1366, 1311, 1274, 1240, 1159, 851 cm$^{-1}$; $^1$H NMR (CDCl$_3$) δ6.77 (bs, 1 H), 6.64 (m, 1 H), 6.39 (bs, 1 H), 6.34 (m, 1 H), 3.73 (bs, 2 H), 1.50 (s, 9 H); $^{13}$C NMR (CDCl$_3$) δ152.1, 147.8, 139.9, 134.8, 109.4, 108.2, 102.6, 80.5, 28.2; Analysis calculated for C$_{11}$H$_{15}$ClN$_2$O$_2$: C, 54.44; H, 6.23; N, 11.54; Cl, 14.61. Found: C, 54.27; H, 6.50; N, 10.96; Cl, 13.99.

Step A-3. A stirred solution of 3-amino-5-chlorophenylcarbamic acid, 1,1-dimethylethyl ester (A-2, 2.06 g, 8.49 mmol) in 170 mL of a 50:50 mixture of methanol and 0.1N aqueous HCl is cooled to 0° C. An aqueous solution of sodium nitrite (1.2 M, 8.5 mL) is added dropwise. After 10 min, sulfamic acid (0.824 g) is added and then sodium azide (0.662 g) in 2.5 mL of water is added dropwise. The reaction mixture is stirred at 0° C. for 15 min, then poured into chloroform (500 mL). The phases are separated and the aqueous layer is extracted with chloroform (2×100 mL). The combined organic layers are dried (MgSO$_4$), filtered and concentrated. The organic residue is purified by flash chromatography using 10% ethyl acetate in hexane as the eluent to afford 1.30 g of 3-azido-5-chlorophenylcarbamic acid, 1,1-dimethylethyl ester. (A-3). IR (neat) 2140 cm$^{-1}$; $^1$H NMR (CDCl$_3$) δ7.17 (m, 1 H), 7.00 (m, 1 H), 6.68 (m, 1 H), 6.53 (bs, 1 H), 1.51 (s, 9 H); $^{13}$C NMR (CDCl$_3$) δ152.0, 141.9, 140.5, 135.6, 114.6, 113.5, 106.8, 81.3, 28.1; Mass Spec (70eV, EI) m/z 268 (parent), 212, 184, 156, 140, 128, 105, 57 (base), 40; Exact Mass calculated for C$_{11}$H$_{13}$ClN$_4$O$_2$: 268.0727. Found: 268.0733.

Step A-4. To a stirred solution of 3-azido-5-chlorophenylcarbamic acid, 1,1-dimethylethyl ester, (A-3, 1.26 g, 4.67 mmol) in 11 mL of dichloromethane is added 11 mL of trifluoroacetic acid. The reaction mixture is stirred at 20°–25° C. for 15 minutes and then concentrated. The residue is diluted with dichloromethane (250 mL) and washed with saturated aqueous NaHCO$_3$ (1×75 mL). The organics are dried (MgSO$_4$), filtered and concentrated. The organic residue is purified by flash chromatography using 20% ethyl acetate in hexane to afford 0.724 g of 3-azido-5-chloroaniline. (A-4, X is Cl). IR (mull) 3474, 3378, 2926, 2141, 2115, 1632, 1603, 1586, 1320, 1268, 1257, 880 cm$^{-1}$; $^1$H NMR (CDCl$_3$) δ6.42 (m, 2 H), 6.17 (m, 1 H), 3.81 (bs, 2 H); $^{13}$C NMR (CDCl$_3$) δ148.5, 142.1, 135.9, 111.6, 109.1,103.5; Mass Spec (70eV, EI) m/z 168 (parent), 140, 107, 78 (base), 63, 52, 37; Exact Mass calculated for C$_6$H$_5$ClN$_4$: 168.0203. Found: 168.0193.

Chart B, Step B-1. To a stirred solution of 3-azido-5-chloroaniline (A-4, 0.706 g, 4.18 mmol) in 6 mL of chloroform, is added diphenyl cyanocarbonimidate (0.997 g, 4.18 mmol). The solvent is allowed to evaporate at a temperature of 75° C. overnight. The resulting solid is triturated with ether and filtered. The solid is recrystallized from ethyl acetate/hexane to afford 0.808 g of N-(3-azido-5-chlorophenyl)-N'-cyanocarbamimidic acid, phenyl ester. (B-1) Mp 193°–194° C. (dec); IR (mull) 3084, 2954, 2925, 2210, 2117, 2104, 1652, 1608, 1581, 1500, 1449, 1438, 1405, 1222, 1197, 1002, 892 cm$^{-1}$; $^1$H NMR (DMSO) δ10.9 (bs, 1 H), 7.45–7.20 (bm, 8 H), 7.07 (bs, 1 H); $^{13}$C NMR (DMSO) δ151.3, 141.5, 138.6, 134.0, 129.8, 126.4, 120.8, 119.4, 116.2, 112.8, 112.5; Analysis calculated for $C_{14}H_9ClN_6O$: C, 53.77; H, 2.90; N, 26.87; Cl, 11.34. Found: C, 53.39; H, 2.71; N, 26.54; Cl, 11.32.

Step B-2. To a stirred suspension of N-(3-azido-5-chlorophenyl)-N'-cyanocarbamimidic acid, phenyl ester (B-1, 0.705 g, 2.25 mmol) in 10 mL of isopropanol is added tert-amylamine (1.0 mL, 9.02 mmol). The reaction mixture is heated at reflux for 4 hours, cooled and concentrated. The organic residue is purified by flash chromatography using 30% ethyl acetate in hexane as the eluent to afford 0.45 g of N-(3-azido-5-chlorophenyl)-N'-cyano-N''-(1,1-dimethylpropyl)guanidine. (B-2) Mp 147°–149° C.; IR (mull) 3325, 3234, 2925, 2159, 2121, 2108, 1611, 1595, 1578, 1558, 1495, 1414, 1228, 853 cm$^{-1}$; 1H NMR (DMSO) δ7.10 (bs, 1 H), 6.80 (m, 1 H), 6.74 (m, 1 H), 6.65 (m, 1 H), 1.55 (q, 2 H, J=7 Hz), 1.14 (s, 6 H), 0.68(t, 3 H, J=7 Hz).; $^{13}$C NMR (DMSO) δ156.3, 141.8, 141.7, 134.5, 116.5, 116.2, 113.4, 109.2, 54.7, 32.3, 26.1, 8.4; Melt Solvate: 0.63% Chloroform; Analysis calculated for $C_{13}H_{16}ClN_7$ plus 0.63% $CHCl_3$:C, 50.81; H, 5.23; N, 31.86; Cl, 12.08. Found: C, 50.73; H, 5.15; N, 31.57; Cl, 12.35.

Example 1(a). Preparation of N-(3-azido-5-chlorophenyl)-N'-cyano-N''-(1,1-dimethyl -2,2,3,3,3-T$_5$-propyl)guanidine (B-2).

CHART B, Preparation of the amine used in Chart B, Step B-2. A micro-hydrogenation apparatus is charged with a solution of 24 mg of 1,1-dimethylpropargylamine hydrochloride in 1 mL of distilled DMF. Ten mg of 10% Pd-C catalyst is suspended over the solution in a glass spoon. The solution is frozen with a liquid $N_2$ bath and the apparatus is alternately degassed at 0.025 torr and filled with dry $N_2$ gas. After three such cycles, the final filling is done with carrier-free tritium gas. The solution is thawed and allowed to reach room temperature (20°–25° C.), the catalyst is added and the mixture is stirred for 3 hours. The mixture is frozen and the excess tritium gas is removed. Labile tritium is removed by alternately adding 2–3 mL of methanol to the thawed mixture and lyophilizing the mixture. This process is repeated three times. The mixture is then passed through a filter consisting of a 3 mL Superclean LC-18 SPE tube and an Acrodisc to remove the catalyst. The filter is washed with 12 mL of methanol in portions. The combined filtrate and washings are lyophilized. The residue was found to contain 28.8 Ci of radioactivity. The $^3$H NMR and $^1$H NMR spectra of this material in methanol-d$_4$ showed that the carbon atoms of the ethyl group in the product were evenly tritiated, with virtually no proton on the terminal carbon. The crude [$^3$H$_5$]-tert-amylamine hydrochloride is dissolved in 2 mL of methanol and used without further purification.

Step B-2. A solution of [$^3$H$_5$]-tert-amylamine hydrochloride in methanol (7.2 Ci in 0.5 mL) is concentrated, and the residue, along with N-(3-azido-5-iodophenyl)-N'-cyanocarbamimidic acid, phenyl ester (B-1, 15.6 mg, 0.05 mmol) is dissolved in 0.5 mL of 1 M triethylamine in isopropanol containing 50 μL of DMF. The resulting clear solution is heated at 84° C. for 6 h in a tightly sealed Reac-T-Vial having a Teflon-lined screw cap. The mixture is then lyophilized and the crude residue purified by means of preparative HPLC using a 4.6 mm I. D.×25 cm stainless steel Supelcosil LC-18 5 μ column. The mobile phase, 650:350:2 (v/v) MeOH:H$_2$O:Et$_3$N, is pumped isocratically at 1.5 mL/min. The eluate is monitored by UV at 254 nm. The fraction containing the desired product is collected and concentrated to remove the methanol. The aqueous residue is lyophilized. The residue is dissolved in methanol for analysis and storage at –70° C. This produces N-(3-azido-5-chlorophenyl)-N'-cyano-N''-(1,1-dimethyl -2,2,3,3,3-T$_5$-propyl)guanidine (B-2) with a specific activity of 284 mCi/mg (89.7 Ci/mmol), radiochemical purity 99.0% by HPLC, 97.6% by TLC (silica gel, 1:9 (v/v) 4M NH$_3$ in MeOH:CH$_2$Cl$_2$).

Example 2. Preparation of N-(3-azido-5-iodophenyl)-N'-cyano-N''-(1,1-dimethylpropyl)guanidine (B-2, X is I).

Chart A, Step A-1. To a stirred solution of 3,5-dinitroiodobenzene (6.65 g, 22.6 mmol, starting material in CHART A) in ethanol (94 mL) is added stannous chloride (51.0 g, 226 mmol). The reaction mixture is heated at 70° C. for 1 hour. The reaction mixture is cooled and poured onto ice (300 cc) and the pH is adjusted to 8 with 10% aqueous sodium hydroxide. A thick white precipitate forms and the reaction mixture is filtered through a pad of celite. The filter cake is first washed with ethyl acetate and then stirred with ethyl acetate (300 mL) for 30 min. The celite mixture is filtered again and filtrates are combined. The phases of the filtrates are separated and the aqueous phase is extracted with ethyl acetate (3×400 mL). The combined organics are dried (Na$_2$SO$_4$), filtered and concentrated. The organic residue is purified by flash chromatography using 50% ethyl acetate in hexane to afford 4.53 g of 5-iodo-1,3-phenylenediamine. (A-1, X is I) Mp=125°–127° C. (dec). IR (mull) 3429, 3312, 3206, 2954, 2925, 2868, 2854, 1632, 1607, 1569, 1472, 1462, 1459, 1198, 984, 810, 675 cm$^{-1}$; $^1$H NMR (CDCl$_3$)δ6.48 (d, 2 H, J=2 Hz), 5.98 (t, 1 H, J=2 Hz), 3.78 (s, 4 H); $^{13}$C NMR (CDCl$_3$) δ148.1, 114.6, 101.0, 94.9; Mass Spec (70eV, EI) m/z 234 (parent), 206, 117, 107 (base), 80, 66, 53, 42; Exact Mass calculated for $C_6H_7IN_2$: 233.9656. Found: 233.9652. Analysis Calculated for $C_6H_7IN_2$: C, 30.79; H, 3.02; N, 11.97; I, 54.22; Found: C, 30.93; H, 2.97; N, 11.71; I, 54.26.

Step A-2. To a stirred solution of 5-iodo-1,3-phenylenediamine (A-1, 4.51 g, 19.27 mmol) in ethyl acetate (27 mL) is added di-tert-butyl dicarbonate (4.20 g, 19.27 mmol). The reaction mixture is stirred at 20°–25° C. overnight and then diluted with ethyl acetate (250 mL). The organics are washed with saturated aqueous bicarbonate (2×50 mL), dried (MgSO$_4$), filtered and concentrated. The residue is purified by medium pressure liquid chromatography using 25% ethyl acetate in hexane as the eluent to afford 4.43 g of 3-amino-5-iodophenylcarbamic acid, 1,1-dimethylethylester. (A-2). Mp 108°–109° C. IR (mull) 3434, 3356, 3322, 2973, 2954, 2925, 2869, 2854, 1699, 1620, 1604, 1599, 1576, 1528, 1473, 1452, 1425, 1300, 1283, 1245, 1170, 1066, 988, 819, 676 cm$^{-1}$; $^1$H NMR (CDCl$_3$) δ7.00 (t, 1 H, J=1.6 Hz) 6.76 (bs, 1 H), 6.67 (m, 2 H), 3.71 (bs, 2 H), 1.48 (s, 9 H); $^{13}$C NMR (CDCL$_3$)δ 152.4, 148.7, 140.2, 118.5, 117.2, 104.3, 94.6, 80.7, 28.2; Mass Spec (70eV, EI) m/z 334 (parent), 278, 261, 234, 206, 151,. 107, 79, 57 (base), 40; Analysis calculated for $C_{11}H_{15}IN_2O_2$: C, 39.54; H, 4.53; N, 8.38; I, 37.98. Found: C, 39.65; H, 4.56; N 8.32; I, 38.09.

Step A-3. A stirred solution of 3-amino-5-iodophenylcarbamic acid, 1,1-dimethylethyl ester (A-2, 4.32 g, 13.0 mmol) in methanol (115 mL) and 1 N aqueous HCl (115 mL) is cooled to 0° C., add 1.2 M aqueous NaNO$_2$ (12.9 mL). The reaction mixture is stirred at 0° C. for 25 min, then sulfamic acid (1.26 g, 13.0 mmol) is added followed by sodium azide (1.01 g, 15.6 mmol) in water (6 mL). Stirring is continued at 0° C. for thirty minutes and then the reaction mixture is poured into chloroform (400 mL). The phases are separated and the aqueous phase is extracted with chloroform (2×150 mL). The combined organics are dried ($MgSO_4$), filtered and concentrated. The organic residue is purified by flash chromatography using 20% ethyl acetate in hexane as the eluent to afford 4.04 g of 3-azido-5-iodophenylcarbamic acid, 1,1-dimethylethyl ester (A-3) as an orange colored oil. This material is used immediately in the next reaction, Step A-4. IR (liquid)3308, 2981, 2119, 2105, 1709, 1691, 1599, 1580, 1537, 1528, 1456, 1451, 1414, 1367, 1276, 1257, 1244, 1160 cm$^{-1}$; $^1$H NMR ($CDCl_3$) δ7.47 (s, 1 H), 7.09 (t, 1 H, J=2 Hz), 7.01 (t, 3 H, J=2 Hz), 6.00 (bs, 1 H), 1.51 (s, 9 H); $^{13}$C NMR ($CDCl_3$) δ152.0, 141.5, 140.4, 123.2, 122.0, 108.1, 94.2, 81.2, 28.0; Mass Spec (70eV, EI) m/z 360 (parent), 304, 276, 248, 232, 205, 149, 131, 105, 77, 57 (base), 40. Exact mass calculated for $C_{11}H_{13}IN_4O_2$: 360.0085. Found: 360.0051.

Step A-4. To a stirred solution of 3-azido-5-iodophenylcarbamic acid, 1,1-dimethylethyl ester (A-3, 4.03 g, 11.2 mmol) in dichloromethane (13 mL) is added trifluoroacetic acid (13 mL). The reaction mixture is stirred at 20°–25° C. for 30 minutes and then carefully poured into a stirred mixture of saturated aqueous bicarbonate (300 mL) and dichloromethane (300 mL). The phases are separated and the organics are dried ($MgSO_4$), filtered and concentrated. The residue is purified by medium pressure liquid chromatography using 20% ethyl acetate in hexane as the eluent to afford 2.43 g of 3-azido-5-iodoaniline (A-4) which is used immediately in the next reaction, CHART B, Step B-1. A small analytical sample is recrystallized from ethyl acetate in hexane. Mp=89°–91° C. IR (mull) 3402, 3299, 2954, 2925, 2869, 2135, 2119, 1596, 1581, 1572, 1570, 1463, 1149, 1304, 1246, 987, 842, 826 cm$^{-1}$; $^1$H NMR ($CDCl_3$) δ6.79 (t, 1 H, J=2 Hz), 6.75 (t, 1 H, J=3 Hz), 6.23 (t, 1 H, J=2 Hz), 3.75 (bs, 2 H); $^{13}$C NMR($CDCl_3$) δ148.5, 141.9, 120.3, 117.7, 104.6, 94.9; Mass Spec (70eV, EI) m/z 260 (parent), 232, 205, 165, 127, 116, 105 (base), 78, 66, 541, 37; Exact mass calculated for $C_6H_5IN_4$: 259.9561. Found: 259.9573. Analysis calculated for $C_6H_5IN_4$; C, 27.71; H, 1.90; N, 21.55; Found C, 27.67; H, 1.90; N, 21.66.

CHART B, Step B-1. To a solution of 3-azido-5-iodoaniline (A-4, 2.42 g, 9.31 mmol) in chloroform (8 mL) is added diphenyl cyanocarbonimidate (2.21g, 9.31 mmol). The solvent is allowed to evaporate at a temperature of 70° C. overnight. The resulting solid is washed with ether, filtered and dried to afford 3.558 g of N-(3-azido-5-iodophenyl)-N'-cyanocarbamimidic acid, phenyl ester (B-1) which is used without further purification. A small analytical sample is recrystallized from ethyl acetate in hexane. Mp=195° C. (dec). IR (mull) 3094, 3078, 2954, 2925, 2867, 2854, 2208, 2121, 2106, 1652, 1600, 1590, 1565, 1504, 1491, 1446, 1433, 1401, 1302, 1219, 1195, 833 cm$^{-1}$; $^1$H NMR (DMSO) δ10.57 (bs (1 H), 7.50 (t, 1 H, J=2 Hz), 7.28 (m, 2 H), 7.10 (m, 5 H); $^{13}$C NMR (DMSO) δ151.4, 141.3, 138.6, 129.9, 128.2, 126.4, 124.6, 120.8, 113.6, 95.0; Mass Spec (70eV, EI) m/z 404 (parent), 376, 249 (base), 222, 207, 194, 155, 145, 128, 118, 103, 94, 77, 65, 51; Exact mass calculated for $C_{14}H_9IN_6O$: 403.9884. Found: 403.9877. Melt solvate: 3.6% ethyl acetate; Analysis calculated for $C_{14}H_9IN_6O$ plus 3.6% $C_4H_8O_2$: C, 42.07; H, 2.49; N, 20.04; Found; C, 41.95; H, 2.25; N, 19.76.

Step B-2. To a stirred suspension of N-(3-azido-5-iodophenyl)-N'-cyanocarbamimidic acid, phenyl ester (B-1, 1.09 g, 2.69 mmol) in isopropanol (20 mL) is added tert-amylamine (0.95 mL, 8.08 mmol). The reaction mixture is heated to reflux for 2.5 hour. The cooled reaction mixture is concentrated and the residue is diluted with ether (50 mL) and washed with 1 N aqueous sodium hydroxide (2×15 ml). The aqueous is extracted with ether (2×30 mL). The combined organics are dried ($MgSO_4$), filtered and concentrated. The organic residue is purified by flash chromatography using 25% ethyl acetate in hexane as an eluent to afford 0.694 g of N-(3-azido-5-iodophenyl)-N'-cyano-N"-(1,1-dimethylpropyl)guanidine (B-2) as a foam. IR (mull) 3310, 3251, 3077, 2954, 2924, 2869, 2854, 2174, 2109, 1603, 1582, 1572, 1497, 1457, 1421, 1408, 1366, 1301, 1231, 844 cm$^{-1}$; $^1$H NMR ($CDCl_3$)δ8.29 (bs, 1 H), 7.33 (t, 1 H, J=2 Hz), 7.24 (t, 1 H, J=2 Hz), 6.83 (t, 1 H, J=2 Hz), 4.64 (bs I H), 1.70 (q, 2 H, J=7 Hz), 1.32 (s, 6 H), 0.84 (t, 3 H, J=7 Hz); $^{13}$C NMR ($CDCl_3$) δ156.7, 142.7, 138.5, 129.0, 125.4, 116.9, 114.2, 94.8, 55.6, 32.9, 26.3, 8.1; Mass Spec (70eV, EI) m/z 397 (parent), 369, 328, 299, 258, 242, 232, 213, 172, 145, 130, 105, 71, 55, 43 (base); Exact mass calculated for $C_{13}H_{16}IN_7$: 397.0514. Found: 397.0532.

Example 2(a). Preparation of N-(3-azido-5-iodo-$^{125}$I-phenyl)-N'-cyano-N"-(1,1-dimethylpropyl) guanidine.

Beginning with the product of Example 2, above (B-2). To a stirred solution of N-(3-azido-5-iodophenyl)-N'-cyano-N"-(1,1-dimethylpropyl)guanidine (B-2, 248 mg, 0.625 mmol) and hexamethylditin (225 mg, 0.688 mmol) in dry tetrahydrofuran is added tetrakis(triphenylphosphine)palladium(0) (21.7 mg, 0.02 mmol). The reaction mixture is heated at reflux for 3 h, then cooled and filtered through a small pad of celite. The filtrate is concentrated and the residue is purified by flash chromatography using 25% ethyl acetate in hexane as the eluent to afford 0.109 g of N-[3-azido-5-(trimethylstannyl)phenyl]-N'-cyano-N"(1,1-dimethylpropyl)guanidine. Mp=134°–136° C. (softens 125° C.). IR (mull) 3414, 3204, 3001, 2954, 2925, 2870, 2854, 2170, 2142, 2116, 1608, 1585, 1565, 1561, 1467, 1414, 1402, 1370, 1310, 1258, 1229, 1199, 857, 767 cm$^{-1}$; $^1$H NMR ($CDCl_3$) δ7.31 (bs, 1 H), 7.04 (d, 2 H, J=2 Hz), 6.76 (t, 1 H, J=2 Hz), 4.66 (bs, 1 H), 1.71 (q, 2 H, J=7 Hz), 1.31 (s, 6 H), 0.82 (t, 3 H, J=7 Hz), 0.33 (s, 9 H); $^{13}$C NMR ($CDCl_3$) δ157.1, 147.6, 141.3, 136.6, 127.7, 124.3, 118.0, 115.1, 55.7, 33.0, 26.6, 8.3; Mass Spec (FAB) m/z 436 (M+1), 420, 408, 392, 338, 332, 292, 280, 165 (base), 71, 43; Exact mass calculated for $C_{16}H_{26}N_7Sn$: 436.1269. Found: 436.1247.

N-[3-Azido-5-(trimethylstannyl)phenyl]-N'-cyano-N"-(1,1-dimethylpropyl)guanidine from above (100 μg in 100 μL of methanol, 0.23 μmoles), Na$^{125}$I (36.4 mCi), 1N HCl (10 μL), and chloramine-T hydrate (100 μg in 100 μL of water, 0.44 μmoles) are combined in 100 μL of 0.2M sodium phosphate buffer (pH 6.8) in a 5 mL Combi v-vial. After 30 minutes at room temperature, the reaction mixture is injected onto a Waters μBondapack RP $C_{18}$ HPLC column and N-(3-azido-5-iodo-$^{125}$I-phenyl)-N'-cyano-N"-(1,1 -dimethylpropyl)guanidine is isolated by elution with acetonitrile/water (0.1% TFA) (20% acetonitrile to 40% acetonitrile over 40 min). This procedure may be performed in any facility suited for radioiodination.

Example 3. Preparation of N-(3-azido-5-iodophenyl)-N'-cyano-N"-(1-(3-fluorophenyl)cyclobutyl)guanidine.

CHART B, Preparation of the amine used in Chart B, Step B-2. A stirred suspension of freshly washed and dried sodium hydride (50% by wt, 9.59 g, 200 mmol) in dry dimethyl sulfoxide (75 mL) under $N_2$ is cooled to 0° C. A mixture of 3-fluorophenylacetonitrile (8.6 mL, 74.0 mmol) and 1,3-dibromopropane (8.3 mL, 81.4 mmol) in ether (40 mL) is then added dropwise over 35 minutes, via cannula.

The resulting orange-red mixture is allowed to stir at 20°–25° C. overnight. The thick reaction mixture is cooled to 0° C. and treated with isopropanol (4 mL). After stirring for 15 minutes, water (64 mL) is added in 10 mL increments and the phases are separated. The aqueous layer is extracted with ether (4×100 mL). The combined organics are washed with water (3×100mL), brine (1×100 mL), dried (MgSO$_4$), filtered and concentrated. The product is distilled at 95° C. (1.0 torr) to afford 7.41 g of 1-(3-fluorophenyl)cyclobutanecarbonitrile. $^1$H NMR (CDCl$_3$) δ7.39 (m, 1 H), 7.19 (m, 1 H), 7.13 (m, 1 H), 7.05 (m, 1 H), 2.81 (m, 2 H), 2.60 (m, 4 H), 2.50 (m, 1 H), 2.12 (m, 1 H); $^{13}$C NMR (CDCl$_3$) δ164.6, 161.3, 142.2, 130.6, 130.5, 123.8, 121.37, 121.32, 115.0, 114.7, 113.0, 112.7, 77.2, 40.9, 39.9, 34.6, 17.0.

A mixture of 1-(3-fluorophenyl)cyclobutanecarbonitrile (7.41 g, 42.3 mmol) and powdered potassium hydroxide (7.0 g, 125 mmol) in ethylene glycol (100 mL) is heated at 150° C. for 7 hours. The cooled reaction mixture is diluted with ice water (140 mL) and extracted with ether (3×100 mL). The combined organics are washed with water (2×35 mL). The combined aqueous washings are cooled to 0° C. and brought to pH 3 with 6 N aqueous hydrochloric acid (30 mL). Nitrogen is bubbled through the solution to give a solid precipitate. The solid is isolated by filtration, washed with water and dried in a vacuum oven at 60° C. for 48 hours to afford 7.04 g of 1-(3-fluorophenyl)cylobutanecarboxylic acid. $^1$H NMR (CDCl$_3$) δ7.27 (m, 2 H), 7.00 (m, 4 H), 2.84 (m, 2 H), 2.48 (m, 2 H), 2.10 (m, 1 H), 1.93 (m, 1 H).

To a stirred solution of 1-(3-fluorophenyl)cyclobutanecarboxylie acid (7.03 g, 36.2 mmol) in toluene (150 mL), under N$_2$, is added diphenylphosphorylazide (10.9 mL, 50.7 mmol) followed by triethylamine (6.5 mL, 47.1 mmol). The reaction mixture is stirred at 20°–25° C. for 15 minutes, 72° C. for 20 minutes, 85° C. for 40 minutes, then finally at 90° C. for 30 minutes. Benzyl alcohol (5.6 mL, 54.3 mmol) is added and the reaction mixture heated overnight at reflux. The cooled reaction mixture is concentrated. The residue is redissolved in toluene (75 mL) and washed successively with 5% aqueous citric acid (2×35 mL), water (2×35 mL), saturated aqueous bicarbonate (2×35 mL) and brine (1×35 mL). The organic layer is dried, (MgSO$_4$), filtered and concentrated. The residue is recrystallized from methyl-tert-butyl ether in hexane to afford 8.26 g of 1-(3-fluorophenyl) cyclobutanecarbamic acid, benzyl ester. Mp 81°–82° C. IR (mull) 3251, 3126, 3113, 3088, 3067, 3043, 3026, 3006, 1706, 1614, 1588 cm$^{-1}$. $^1$H NMR (CDCl$_3$) δ7.23 (m, 8 H), 6.92 (m, 1 H), 5.35 (bs, 1 H), 5.01 (bs, 2 H), 2.53 (bs, 4 H), 2.11 (m, 1 H), 1.84 (m, 1H); Analysis calculated for C$_{18}$H$_{18}$FNO$_2$: C, 72.22; H, 6.06; N, 4.68. Found: C, 72.22; H, 6.20; N, 4.50.

A stirred solution of 1-(3-fluorophenyl)cyclobutanecarbamic acid, benzyl ester (8.25 g, 27.6 mmol) and ammonium formate (5.04 g, 79.9 mmol) in methanol (120 mL) under N$_2$ is cooled to 15° C. Ten percent palladium on carbon (1.5 g) is added portionwise over 10 minutes. The reaction mixture is stirred at 15° C. for 45 minutes, then filtered through a small pad of celite. The filter cake is washed with methanol. The filtrate is concentrated. The resulting white solid is partitioned between dichloromethane (150 mL) and saturated aqueous bicarbonate (150 mL). The phases are separated and the aqueous phase extracted with dichloromethane (3×75 mL). The combined organics are washed with saturated aqueous bicarbonate (1×100 mL), water (1×100 mL) and brine (1×100 mL), dried (MgSO$_4$), filtered and concentrated. The organic residue is purified by flash chromatography using 2.5% methanol (saturated with ammonia) in dichloromethane as the eluent to afford 3.77 g of 1-(3-fluorophenyl)cyclobutanamine. This product is the amine used in Step B-2. $^1$H NMR (CDCl$_3$) δ7.32 (m, 1 H), 7.19 (m, 1 H), 7.09 (m, 1 H), 6.94 (m, 1 H), 2.54 (m, 2 H), 2.12 (m, 3 H), 1.80 (m, 1 H), 1.70 (s, 2 H); $^{13}$C NMR (CDCl$_3$) δ164.6, 161.3, 151.99, 151.90, 129.9, 129.8, 120.54, 120.50, 113.3, 113.0, 112.2, 111.9, 58.8, 36.9, 14.1.

Step B-2. To a stirred suspension of N-(3-azido-5-iodophenyl)-N'-cyanocarbamimidic acid, phenyl ester (B-1, 472 mg 1.16 mmol) in isopropanol was added 1-(3-fluorophenyl)cyclobutanamine (227 mg, 1.40 mmol). The reaction mixture was heated in a sealed tube at 82° C. overnight. The cooled reaction mixture was concentrated. The residue was purified by medium pressure liquid chromatography using 30% ethyl acetate in hexane as the eluent to afford 0.257 g of N-(3-azido-5-iodophenyl)-N'-cyano-N''-[1-(3-fluorophenyl)cyclobutyl]guanidine. (B-2). Mp=171°–173° C. (dec). IR (mull) 3195, 3135, 3078, 3002, 2953, 2925, 2854, 2188, 2110, 1614, 1608, 1587, 1573, 1542, 1448, 1440, 1430, 1365, 1309, 1292, 1245, 1221, 1162, 1041, 874 cm$^{-1}$; $^1$H NMR (CDCl$_3$) δ7.42 (m, 1 H), 7.26 (m, 2 H), 7.17 (m, 2 H), 7.06 (m, 1 H), 6.78 (m, 1 H), 2.59 (m, 4 H), 2.15 (m, 1 H), 2.00 (m, 1 H), 1.61 2, 2 H); $^{13}$C NMR (CDCl$_3$) δ156.4, 138.0, 131.3, 124.9, 120.6, 116.3, 114.7, 114.4, 112.8, 112.5, 94.9, 59.6, 34.7, 14.8; Mass Spec (FAB) m/z 476 (M+1), 448, 434, 421, 350, 328, 300, 273, 216, 173, 149 (base). Exact mass calculated for C$_{18}$H$_{16}$FIN$_7$: 476.0498. Found: 476.0514. Analysis calculated for C$_{18}$H$_{15}$FIN$_7$: C, 45.49; H, 3.18; N, 20.63. Found: C, 45.23; H, 3.16; N, 20.37.

Example 3(a). Preparation of N-(3-azido-5-iodo-125I-phenyl)-N'-cyano-N''-[1-(3-fluorophenyl) cyclobutyl]guanidine.

Begin with product of Example 3, (B-2). To a stirred solution of N-(3-azido-5-iodophenyl) -N'-cyano-N''-[1-(3-fluorophenyl)cyclobutyl]guanidine (B-2, 63.1 mg, 0.133 mmol) and hexamethylditin (47.8 mg, 0.146 mmol) in dry tetrahydrofuran (7 mL) is added tetrakis(triphenylphosphine)palladium(0) (4.6 mg, 0.004 mmol). The reaction mixture is heated at reflux for 3 hours, cooled and concentrated. The organic residue is purified by flash chromatography using 30% ethyl acetate in hexane as the eluent to afford 23.3 mg of N-[3-azido -5-(trimethylstannyl)phenyl]-N'-cyano-N''-(1,1-dimethylpropyl)guanidine. IR (mull) 3416, 3210, 3146, 3024, 2953, 2923, 2868, 2854, 2191, 2171, 2119, 1603, 1583, 1568, 1546, 1483, 1466, 1441, 1408, 1400, 1356, 1305, 1257, 1231, 1149, 856 cm$^{-1}$; $^1$H NMR (CDCl$_3$) δ7.38 (m, 1 H), 7.26 (m, 2 H), 7.13 (m, 1 H), 6.98 (m, 1 H), 6.79 (m,1 H), 2.59 (m, 2 H), 2.52 (m, 2 H), 2.11 (bm, 1 H), 1.97 (bm, 1 H), 1.59 (s, 2 H), 0.31 (s, 9 H); $^{13}$C NMR (CDCl$_3$) δ156.9, 136.4, 131.3, 124.7, 121.1,116.9, 114.7, 114.4, 113.0, 112.7, 59.9, 34.9, 15.1; Analysis calculated for C$_{21}$H$_{24}$FN$_{71}$Sn; C, 49.25; H, 4.72; N, 19.14; Found: C, 49.06; H, 4.82;, N, 18.81.

N-[3-azido-5-(trimethylstannyl)phenyl]-N'-cyano-N''-(1,1-dimethylpropyl)guanidine (100 μg in 100 μL methanol, Na$^{125}$I (12.2 mCi), and chloramine-T (100 μg in 100 μL water) are combined in 100 μL of 0.2 M sodium phosphate buffer (pH 6.8) in a 5 mL Combi v-vial. After 30 minutes at room temperature, the reaction mixture is injected onto a Waters μBondapak RP C$_{18}$ HPLC column from which N-(3-azido-5-iodo-$^{125}$I-phenyl)_N'-*cyano-N*''-[1-(3-fluorophenyl)cyclobutyl]guanidine is isolated by elution with 60% methanol in 0.1% aqueous TFA. This procedure may be performed in any facility suited for radioiodination.

Example 4. Preparation of N-(3-azido-5-iodophenyl)-N'-cyano-N''-(1,1dimethylethyl)guanidine.

CHART B, Step B-2. Using the same procedure as described in Example 2, N-(3-azido-5-iodophenyl)-N'-cyano-N"-(1,1-dimethylethyl)guanidine (B-2) is prepared from N-(3-azido-5-iodophenyl)-N'-cyanocarbamimidic acid, phenyl ester (B-1) and tert-butylamine. Mp.=163°–165° C. (dec). IR (mull) 3407, 3311, 3068, 2954, 2925, 2869, 2187, 2164, 2127, 2101, 1611, 1585, 1572, 1547, 1495, 1477, 1465, 1448, 1408, 1369, 1310, 1231, 846 cm$^{-1}$; $^1$H NMR (DMSO) δ9.13 (s, 1 H), 7.25 (s, 1 H), 7.19 (t, 1 H, J=2 Hz), 7.05 (t, 1 H, J=2 Hz), 6.75 (t, 1 H, J=2 Hz), 1.26 (s, 9 H); $^{13}$C NMR (DMSO) δ155.4, 141.9, 141.5, 125.4, 121.9, 115.3, 110.3, 95.7, 52.1, 28.6; Mass Spec (70eV, EI) m/z 355, 299, 257, 228, 172 (base), 145, 130, 118, 105, 89, 78, 68, 57, 40; Analysis calculated for $C_{12}H_{14}IN_7$; C, 37.61; H, 3.68, N, 25.59; Found; C, 37.92; H, 3.74; N, 24.98.

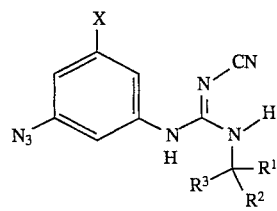

Formula I where

X is Halogen, $R_1$ is H, or $C_{1-3}$ alkyl;

$R_2$ is H, or $C_{1-3}$ alkyl; or

CHART C
Compound Structures and Names

| Example No. | Structure | Name |
| --- | --- | --- |
| Example 1 | 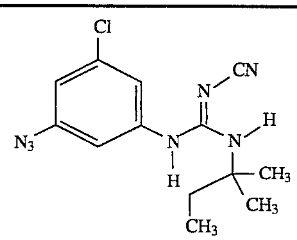 | Guanidine, N-(3-azido-5-chlorophenyl)-N'-cyano-N"-(1,1-dimethylpropyl)- |
| Example 2 | 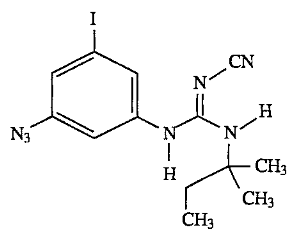 | Guanidine, N-(3-azido-5-iodophenyl)-N'-cyano-N"-(1,1-dimethylpropyl)- |
| Example 3 | 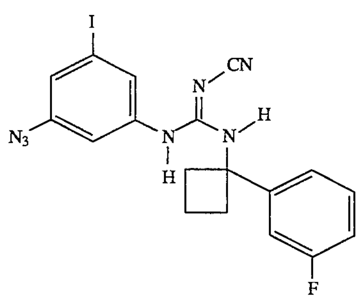 | Guanidine, N-(3-azido-5-iodophenyl)-N'-cyano-N"-(1-(3-fluorophenyl)-cyclobutyl)- |
| Example 4 | 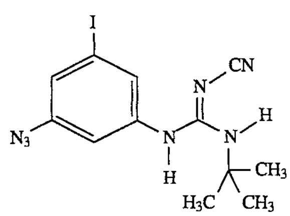 | Guanidine, N-(3-azido-5-iodophenyl)-N'-cyano-N"-(1,1-dimethylethyl)- |

We claim:

1. A compound represented by the following structural formula, $R_1$ and $R_2$ are joined together to form $C_{3-6}$ cycloalkyl, or $C_{3-6}$ cycloalkyl optionally substituted with $C_{1-4}$ alkyl;

$R_3$ is $C_{1-6}$ alkyl.

2. A compound of claim 1 where, $R_1$ is $C_{1-2}$ alkyl;

$R_2$ is $C_{1-2}$ alkyl; or $R_1$ and $R_2$ are joined together to form $C_{4-5}$ cycloalkyl;

$R_3$ is $C_{2-3}$ alkyl; and

X is chloro or iodo.

3. A compound of claim 2 selected from the group consisting of
   a) N-3-azido-5-chlorophenyl)-N'-cyano-N''-(1,1-dimethyl-propyl)guanidine,
   b) N-3-azido-5-iodophenyl)-N'-cyano-N''-(1,1-dimethyl-propyl)guanidine, and
   c) N-(3-azido-5-iodophenyl)-N'-cyano-N''-(1.1-dimethyl-ethyl)guanidine.

4. A compound represented by the following structure

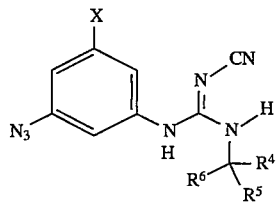

where

X is Halogen;

$R_4$ is H, or $C_{1-3}$ alkyl;

$R_5$ is H, or $C_{1-3}$ alkyl; or $R_4$ and $R_5$ are joined together to form $C_{3-6}$ cycloalkyl, or $C_{3-6}$ cycloalkyl optionally substituted with $C_{1-4}$ alkyl;

$R_6$ is a $C_{6-12}$ aryl optionally substituted with $C_{1-2}$ alkyl, or 1–3 Halogens.

5. A compound of claim 4 where, $R_4$ is $C_{1-2}$ alkyl;

$R_5$ is $C_{1-2}$ alkyl; or $R_4$ and $R_5$ are joined together to form a $C_{4-5}$ cycloalkyl.

6. A compound of claim 5, where, $R_6$ is a $C_6$ aromatic ring optionally substituted with one or two of any combination of $C_{1-2}$ alkyl, fluorine and chlorine.

7. A compound of claim 6 where $R_4$ and $R_5$ are joined together to form a $C_4$ cycloalkyl and X is chloro or iodo.

8. A compound of claim 7 which is,
   a) N-(3-azido-5-iodophenyl)-N'-cyano-N''-(1-(3-fluorophenyl)-cyclobutyl)guanidine.

* * * * *